Figure 1A:
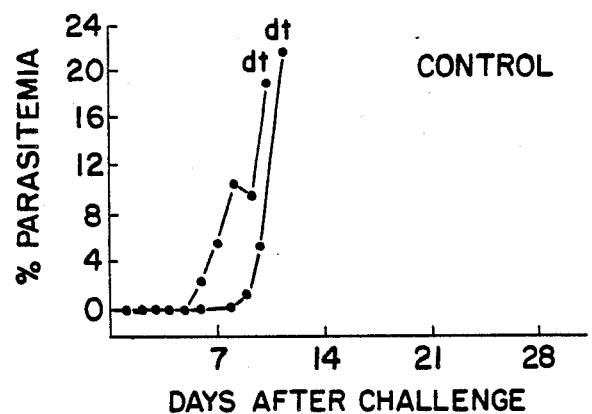

United States Patent [19]

Siddiqui

[11] Patent Number: 4,897,354
[45] Date of Patent: Jan. 30, 1990

[54] MONOCLONAL ANTIBODY-SPECIFIC MEROZOITE ANTIGENS

[75] Inventor: Wasim A. Siddiqui, Honolulu, Hi.

[73] Assignee: University of Hawaii, Honolulu, Hi.

[21] Appl. No.: 891,209

[22] Filed: Jul. 28, 1986

[51] Int. Cl.$^4$ .................. C12N 5/00; C12N 15/00; C12P 21/00
[52] U.S. Cl. .................. 435/240.27; 435/172.2; 435/70.21; 530/387; 935/104; 935/110
[58] Field of Search ............... 435/68, 172.2, 240.27; 530/387; 935/104, 110

[56] References Cited

U.S. PATENT DOCUMENTS 4,466,917  8/1984  Nussenzeig .

FOREIGN PATENT DOCUMENTS 2145092A  3/1985  United Kingdom .
2154542A  9/1985  United Kingdom .

OTHER PUBLICATIONS

Perrin, L. H., et al. Nature, vol. 289, pp. 301–303, 1981.
McBride, J. S., et al. J. Exp. Med., vol. 161, pp. 160–180, 1985.
Howard, R. J., Molecular & Biochem. Parasitology, 11, pp. 349–362, 1984.
Pirson, P. H. et al, J. Immunol., vol. 134, pp. 1946–1951, 1985.
Holder, A. A., et al. J. Exp. Med., vol. 156, pp. 1528–1538, 1982.
L. H. Perrin et al., *Clin. Exp. Immunol.*, 41, 91–96 (1980).
R. R. Freeman et al., *J. Exp. Med.*, 158, 1647–1653 (1983).
A. A. Holder et al., *J. Exp. Med.*, 160, 624–629 (1984).
R. Hall et al., *Mol. Biochem. Parasit.*, 11, 61–80 (1984).
R. Schmidt-Ullrich et al., *J. Exp. Med.*, 163, 179–188 (1986).
R. Hall et al., *Nature*, 31, 379–382 (1984).
L. H. Perrin et al., *J. Exp. Med.*, 160, 441–451 (1984).
F. Ardeshir et al., *PNAS*, 82, 2518–2522 (Apr. 1985).
F. Ardeshir et al., *Vaccines 85*, 35–38 (1985).

*Primary Examiner*—Christine M. Nucker
*Assistant Examiner*—Karen I. Krupen
*Attorney, Agent, or Firm*—Davis Hoxie Faithfull & Hapgood

[57] ABSTRACT

Disclosed herein is a *P. falciparum* merozoite antigenic polypeptide of approximate molecular weight 185,000. The polypeptide and processing fragments are specific to, and isolable using, a monoclonal antibody produced by hybridoma cell line HB 9148. The polypeptides are useful in immunizing against malaria.

4 Claims, 1 Drawing Sheet

MONOCLONAL ANTIBODY-SPECIFIC MEROZOITE ANTIGENS

This invention was made with government support under Grant No. DPE-0453-A-00-4039-00 awarded by the Agency for International Development. The government has certain rights in this invention.

BACKGROUND OF THE INVENTION

This invention relates to antigenic *P. falciparum* merozoite surface polypeptides of approximate molecular weight 185,000 and processing fragments thereof. In particular, the invention relates to such polypeptides isolated by monoclonal antibody 5.2 of the invention. The polypeptides have use as vaccines.

Malaria is a serious health problem in many parts of the world. The disease is caused by a mosquito-borne parasite of the genus Plasmodium. Of greatest concern to humans are the *Plasmodium falciparum* and *Plasmodium vivax* species of the parasite.

The Plasmodium parasite has a complex life cycle. The parasite is introduced into the human body by the mosquito in the sporozoite form. The sporozoite travels to the human liver where it differentiates into the merozoite form of the parasite. Each merozoite, upon release from the liver, invades a red blood cell and goes through a series of stages (ring, trophozoite, schizont), eventually resulting in the formation and release of a large number (10-30) of merozoites. These merozoites then attack other red blood cells and the process continues unless arrested by medication of the body's immune system. As used herein, the term "asexual red blood cell stage parasite" shall be taken to embrace the various forms in which the parasite exists within the red blood cell, including merozoite, ring, trophozoite and schizont stages.

There have been a number of reports of work directed toward the possibility of developing a vaccine for either the sporozoite or merozoite stage of the malaria parasite. Work in the sporozoite area is disclosed in, e.g., U.S. Pat. No. 4,466,917 and UK Patent Application No. 2,145,092A (published Mar. 20, 1985).

Workers studying the merozoite in *P. falciparum* have reported a class of polypeptides in merozoites (and their schizont precursors) with molecular weights varying over the range of 185,000 to 200,000 (185K to 200K). The variation in reported molecular weights is in part a reflection of the fact that relative molecular weight ($M_r$) estimates using SDS-PAGE are approximations, but the variation is also attributable to real differences in the polypeptides isolated from different malaria isolates. Molecules within this class of polypeptides have been referred to at various times, inter alia, as pf195, P195, P190, gp185, P200 and polymorphic schizont antigens (PSA). Polypeptides within this class have been reported on occasion to be surface molecules, to be antigenic in nature, and to be precursors for surface fragments of smaller molecular weight.

There have been a number of reports of work with monoclonal antibodies specific to polypeptides within the class of 185-200K *P. falciparum* merozoite polypeptides. L. H. Perrin et al., *Clin. Exp. Immunol.*, 41, 91-96 (1980) reported immunoprecipitation of 195K 35-S-methionine protein (Senegal isolate) using monoclonal antibody 2B6. The protein did not inhibit parasite growth in vitro. A. A. Holder et al., *J. Exp. Med.*, 156, 1528-1538 (1982) reported that monoclonal antibody 89.1 identified a 195K merozoite surface coat precursor protein (Wellcome-Lagos isolate). R. R. Freeman et al., *J. Exp. Med.*, 158, 1647-1653 (1983) reported that the 195K precursor protein identified by monoclonal antibody 89.1 is processed to an 83K surface fragment. A. A. Holder et al., *J. Exp. Med.*, 160, 624-629 (1984) reported that the 195K precursor protein identified by monoclonal antibody 89.1 gave rise to 42K and 19K surface fragments. R. J. Howard et al., *Mol. Biochem. Parasit.*, 11, 349-362 (1984) reported the immunoprecipitation of a glycosylated 195K protein (St. Lucia isolate) with monoclonal antibodies PF27H10.19 and PF23H7.1. R. Hall et al., *Mol. Biochem. Parasit.*, 11, 61-80 (1984) reported that monoclonal antibody 2.2 recognized a constant epitope while monoclonal antibody 7.3 recognized a variable epitope on a 190K merozoite surface protein (KI Thai isolate). P. H. Pirson et al., *J. Immunol.*, 134, 1946-1951 (1985) reported that monoclonal antibody 5B1 specific to a processed 200K glycoprotein (Gambia isolate) partially inhibited parasite growth in vitro. J. McBride et al., *J. Exp. Med.*, 161, 160-180 (1985), working primarily with a Thai isolate and a panel of strain-specific monoclonal antibodies, reported that *P. falciparum* consists of a number of antigenically diverse strains. They reported a "family" of polymorphic schizont antigens of $M_r$ 190-200K. R. Schmidt-Ullrich et al., *J. Exp. Med.*, 163, 179-188 (1986), working with hybridomas KJ7-2C11D and KD8-2B2D, reported monoclonal antibodies binding to a 195K polypeptide (Gambia K1 isolate).

There have also been reports of attempts to demonstrate in vivo protection in immunization experiments using polypeptides from the class of merozoite 185-200K polypeptides. R. Hall et al., *Nature*, 31, 379-382 (1984) reported the results of an experiment in which three Saimiri monkeys were immunized with 190K polypeptide (from the Thai isolate K1 of *P. falciparum*) in Freund's complete adjuvant. The polypeptide used in the immunization was isolated using monoclonal antibody 7.3. Upon heterologous challenge with *P. falciparum* (Palo Alto strain), two of the monkeys developed parasitemias of from 5 to 10% before subsequently controlling the infection without drug treatment. The third monkey developed a parasitemia of greater than 20% and was drug treated. There was no increase in the prepatent period relative to the controls. At page 379 the authors described their work as follows: "Immunization with the affinity-purified native protein modifies the course of infection by the parasite."

In other work, L. H. Perrin et al., *J. Exp. Med.*, 160, 441-451 (1984) reported the results of an experiment in which four Saimiri monkeys were immunized with polypeptides eluted from the 200K region of SDS-PAGE gels containing total *P. falciparum* (SGE2 Zaire isolate) polypeptides isolated by human sera. The polypeptides were not isolated or purified with monoclonal antibodies. Each monkey was immunized three times (once in Freund's complete adjuvant and twice in Freund's incomplete adjuvant) with polypeptides from the 200K region of the gel. Upon heterologous challenge with *P. falciparum* (Uganda-Palo Alto strain FUP), one monkey had a peak parasitemia of 11%; one of 6%; and two at a level described at page 445 as being "less than 3%" (the symbol for "less than" is used in the original). For each monkey the parasitemia eventually dropped off to a low level. In each monkey there was an increase in the prepatent period relative to the controls. See FIG. 3 of Perrin et al. at page 446.

The prior art shows the absence of, and the need for, a merozoite polypeptide which can be used in immunization to provide protection against P. falciparum parasitemias of the low levels associated with the symptoms of malaria. In humans the onset of fever and chills caused by malaria occurs at parasitemia levels of 0.5% or less; mortality can occur in non-immunes at levels of 2% parasitemia. Parasitemia is defined as the number of malaria-infected erythrocytes per 100 erythrocytes. It is measured by taking a blood sample from the infected animal or person, preparing stained slides, and reading the slides under the microscope.

SUMMARY OF THE INVENTION

In accordance with the invention a method is provided for obtaining an antigenic *P. falciparum* asexual red blood cell stage polypeptide of approximate molecular weight 185,000 which has use in providing protective immunity. The method comprises isolating *P. falciparum* red blood cells containing such parasites; isolating the protein fraction from said isolated parasites; and isolating a polypeptide fraction comprising an antigenic polypeptide of approximate molecular weight 185,000 based on preferential binding to a monoclonal antibody produced by hybridoma cell line HB 9148. The invention further comprises a method of conferring protective immunity against malaria by immunization using the antigenic polypeptide of approximate molecular weight 185,000 obtained as described above. In addition the invention comprises the antigenic polypeptide, the monoclonal antibody specific to the antigenic protein, hybridoma cell line HB 9148 which produces the monoclonal antibody, and vaccines comprising the antigenic polypeptide. The invention also comprises antigenic polypeptide processing fragments of the 185,000 polypeptide which are specific to a monoclonal antibody produced by hybridoma cell line HB 9148 (in particular fragments of approximate molecular weight 152,000, 121,000 and 83,000) and vaccines comprising any one or more of such processing fragments, with or without the 185,000 polypeptide.

The invention provides a means of conferring protective immunity against malaria challenge to an extent not available with prior art methods and not available in the absence of the monoclonal antibodies of the invention.

BRIEF DESCRIPTION OF THE DRAWING

FIG. 1 is a graphic depiction of protective immunity conferred (in terms of % parasitemia) against challenge in a host animal immunized with antigenic polypeptides of the invention, (FIG. 1*b*) as compared to a non-immunized control (FIG. 1*a*).

DETAILED DESCRIPTION

The antigenic polypeptide of the invention of approximate molecular weight 185,000 (referred to below on occasion as the 185K polypeptide) is obtained from *P. falciparum* using traditional separation steps followed by separation using the monoclonal antibody of the invention (monoclonal antibody 5.2). The *P. falciparum* Uganda Palo Alto (FUP) isolate, available to workers in the field, is a preferred source material ("FUP" is an abbreviation for Falciparum Uganda-Palo Alto strain). Other isolates containing monoclonal antibody 5.2-specific polypeptides can also be used as source material. A preferred separation approach is the culturing of red blood cell stage parasites in an in vitro system in ways known in the art, followed by separation of the parasite from infected erythrocyte cells using known methods for red blood cell lysis. Lysis preferably takes place when the parasites are present in relatively equal proportions of rings, trophozoites and schizonts. Parasites are isolable after lysis using known methods, e.g., centrifugation. The protein fraction of the parasites is then isolated using known methods, e.g., chemical extraction. The antigenic polypeptide of the invention is obtained from the protein fraction using monoclonal antibody 5.2. A preferred technique is to pass the protein fraction through immunoabsorbents containing monoclonal antibody 5.2. The polypeptide fraction specific to monoclonal antibody 5.2 is isolated by appropriate washings and elutions in ways known to those skilled. The collected fraction containing the polypeptide of the invention may be further purified as desired. The collected fraction initially contains not only the antigenic polypeptide of approximate molecular weight 185,000 but also, in smaller quantities, processing fragments of the 185K polypeptide which contain antigenic sites to which MAb 5.2 is specific. Such fragments include polypeptides of approximate molecular weights 152K, 121K and 83K. If desired, the 185K polypeptide may be separated from its processing fragments using known methods for separation based on molecular weight differences, e.g., dialysis.

The hybridoma cell line of the invention, cell line 5.2, was produced by fusion of myeloma cells with spleen cells from mice immunized with schizont-enriched *P. falciparum* (strain FUP), using known methods. See Example 1. Cell line 5.2 is on deposit with the American Type Culture Collection (ATCC) as ATCC deposit number HB 9148 and shall be referred to herein in terms of its ATCC number.

The monoclonal antibody ("MAb") of the invention, MAb 5.2, was produced by cell line HB 9148 and purified using known methods. See Example 1. MAb 5.2 is specific to (i.e., preferentially binds to) the antigenic polypeptides of the invention, in particular, the polypeptides of approximate molecular weight 185K and its processing fragments derived from the Uganda Palo Alto (FUP) Isolate of *P. falciparum*. MAb 5.2 is of immunological type $IgG_{2b}$. MAb 5.2 has application in isolating the polypeptides of the invention for use in vaccines. MAb 5.2 also has use as a diagnostic to assay for the presence, in vivo or in vitro, of the malaria parasite. In addition, MAb 5.2 has use as a curative or therapeutic for clinical purposes of binding to and inactivating or removing malaria parasite.

The polypeptide of the invention of approximate molecular weight 185,000, while in the same molecular weight class as other known merozoite surface polypeptides, is different from and substantially improved over known polypeptides as shown by its effectiveness in conferring protective immunity. As stated, in humans *P. falciparum* infection can lead to the onset of disease symptoms (e.g., fever and chills) at parasitemia levels of 0.5% or less; mortality can occur at levels of 2.0% in non-immunes. As shown in Example 4, the polypeptide of the invention when administered immunologically is capable of conferring protective immunity with a peak parasitemia level lower than either of the above levels in the presence of a *P. falciparum* challenge of potentially lethal proportions. The data presented herein provide direct evidence that the monoclonal-antibody isolated polypeptide of the invention can induce complete protective immunity to a lethal, virulent human malaria parasite.

The 185K polypeptide of the invention, with or without MAb 5.2-specific polypeptide processing fragments thereof, may be used as a vaccine in accordance with known methods of vaccine administration. Less preferably, one or more of the MAb 5.2-specific processing fragments (i.e., alone or in combination) may also be used as a vaccine in the absence of the 185K polypeptide. The polypeptides may be used in a variety of adjuvants or carriers, including Freund's complete adjuvant, Freund's incomplete adjuvant, or other adjuvants as will be understood by those skilled in the art. Pharmaceutically effective adjuvants are preferred.

The polypeptide of the invention may be used to protect against homologous or heterologous challenge. Homologous challenge is a challenge where both the challenge inoculum and polypeptide antigen are derived from the same strain of parasite. In the case of heterologous challenge, the source of challenge inoculum and polypeptide antigen are derived from two different strains of parasites. Indirect fluorescence antibody tests using MAb 5.2 with a variety P. falciparum isolates showed that all cross-reacted with MAb 5.2. See Example 5.

The polypeptide of the invention may also be used as a means to produce antibodies or monoclonal antibodies of use, as described above, diagnostically or therapeutically.

The invention embraces the polypeptide as the native form (i.e., derived from natural parasite), as a modification of the native form, or as a synthetic (e.g., recombinant) counterpart of either.

EXAMPLES

Example 1 Hybridoma Preparation and MAb 5.2 Isolation

Hybridomas were produced by fusion of spleen cells from BALB/c mice immunized with schizont-enriched *P. falciparum*, FUP isolate, with P3x63Ag8.653 myeloma cells (Kearney et al., *J. Immunol.*, 123, 1548–1550, 1979). Hybridomas were screened by solid phase radioimmunoassay; S.C. Kan et al., *Infect Immun.*, 43, 276–282 (1984). Positives were double cloned and ascites produced. Monoclonal antibody 5.2, produced by hybridoma cell line code number HB 9148, stained schizonts and free merozoites by indirect immunofluorescence on acetone-fixed parasites. The pattern was even, linear staining of the parasite surface. Monoclonal antibody 5.2 (IgG$_{2b}$) was purified on Protein-A SEPHAROSE TM (SEPHAROSE is a trademark for beaded, crosslinked agarose), and high capacity immunoabsorbents were prepared; C. Schneider, *J. Biol. Chem.*, 57, 10766–10769 (1982). For comparison purposes immune IgG from previously vaccinated and protected Aotus monkeys was covalent bonded to Protein-A SEPHAROSE TM.

Example 2 Isolation of Polypeptide Using MAb 5.2

A *P. falciparum* Uganda Palo Alto (FUP) K+ (monkey passaged) isolate was grown in a semi-automated in vitro culture system, K. L. Palmer et al., *J. Parasitol.*, 68, 1180–1183 (1982). In different trials, the parasites were kept in culture as long as 8 weeks and as short as 2 weeks. K. M. Yamaga et al., *Exp. Parasitol.*, 58, 138–146 (1984). Approximately $8 \times 10^{11}$ infected erythrocytes containing approximately 33% each of rings, trophozoites and schizonts, were lysed with 0.013% saponin, and centrifuged parasites were extracted with 7 volumes 1% NP-40, 10 mM iodoacetamide, 5 mM EGTA, 5 mM EDTA, and 1mM phenylmethylsulfonyl fluoride in pH 8.0 borate-buffered saline. About 500 mg crude protein (Bio-Rad Protein Assay) was obtained. The extract was divided into two aliquots and each was supplemented with 35-S-methionine labeled polypeptides. One aliquot was passed serially through 3 ml monoclonal antibody 5.2 and immunoabsorbent, while the other aliquot was passed through immune Aotus IgG immunoabsorbent. The columns were washed with 0.5 M NaCl-borate buffer, and eluted with 50 mM diethylamine, pH 11.5, containing 5 mM iodoacetamide, 1 mM EDTA, and 1 mM EGTA, and 0.1% NP-40. Collected fractions were neutralized with M Tris-HCl, pH 8.0, and the peak radioactive tubes pooled and dialyzed against pH 8.0 borate-saline. Immune Aotus IgG isolated 1.8 mg polypeptides, while monoclonal antibody 5.2 immunoabsorbent isolated 0.62 mg polypeptides.

Example 3 Immunological Characteristics of Sera in Monkeys Immunized With MAb 5.2-Isolated Polypeptide Sodium-dodecyl sulfate polyacrylamide gel electrophoresis was conducted in 7.5% polyacrylamide gel for 35-S-methionine labelled *P. falciparum* FUP polypeptides immunoprecipitated by prechallenge sera from vaccinated Aotus monkeys. Serum samples were taken 14 days after the final immunization from three monkeys, each immunized with 100 ug of monoclonal antibody 5.2-isolated polypeptide (see Example 2) three times at 21d intervals in Freund's complete adjuvant; the mycobacterium content was successively halved to reduce granulomata. The serum samples were used to immunoprecipitate the metabolically labeled polypeptides. In the FUP isolate, monoclonal antibody 5.2 isolated a 185K precursor protein and its 152K, 121K, and 83K polypeptides among other smaller processing fragments. By comparison, monoclonal antibody 89.1 (e.g., R. R. Freeman et al., *J. Exp. Med.*, 160, 624–629, 1984), generously supplied to us by Dr. R. R. Freeman (Wellcome Biotechnology, Ltd.), while immunoprecipitating the same or similar molecular weight precursor polypeptide from the FUP isolate, displayed marked differences in monoclonal antibody-defined epitopes. MAb 5.2 bound epitopes on 152K, 121K, 105K, 83K, 29K and 26K processing fragments, while MAb 89.1 bound epitopes on 152K, 83B, and 60K processing fragments. Thus, although the two monoclonal antibodies immunoprecipitated the same or similar precursor, they are distinguishable based upon the determinants recognized and precipitated.

By indirect immunofluorescence on acetone-fixed parasites, the individual reciprocal antibody titers for MAb 5.2 were 4096, 8192, and 8192. In addition, a pool of the three serum samples localized antigens exclusively on the merozoite surface by immunoelectronmicroscopy.

Example 4 Immunization With MAb 5.2 - Isolated Polypeptide

Eleven *Aotus lemurinus griseimembra* (karyotype II and III) monkeys were used in a vaccination experiment. Three Aotus monkeys were immunized three times with the MAb 5.2-isolated 185K polypeptide and processing fragments in Freund's complete adjuvant. The specificities of the sera are described above in Example 3. The monkeys were challenged with $7 \times 10^5$ virulent, homologous K+ (monkey-passaged) FUP parasites. In aotus monkeys immunized with MAb 5.2-isolated 185K polypeptide and its processing fragments, no parasites could be detected over a 60-day period in thick blood films. Approximately one hundred microscope fields for each blood sample slide per day for sixty continuous days were examined and no parasites were detected (limit of detection 0.001%). The absence of any breakthrough of parasitemia over a sixty day period indicated solid immunity and complete protection of the monkeys. Two unimmunized control Aotus monkeys showed a rapid rise in parasitemia and were drug-treated to prevent fatal infection.

Figure 1B:
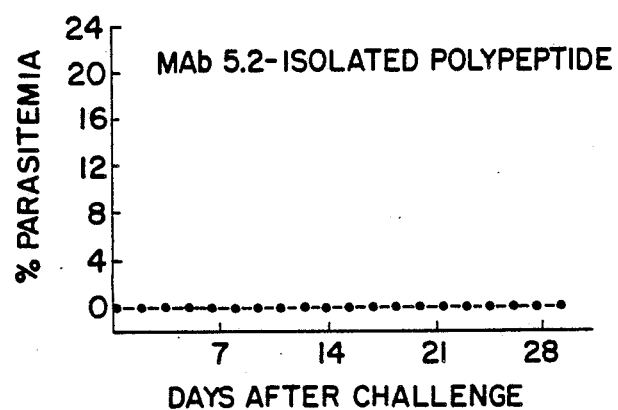

FIG. 1 shows the course of infection of virulent, monkey-passaged P. falciparum (FUP) in *Aotus lemurinus griseimembra* (karyotype II and III) monkeys. Two unimmunized Aotus monkeys had high parasitemias and were drug-treated (dt) to prevent death (control group). As stated, all three Aotus immunized with the native merozoite surface protein were completely protected and no patent parasitemia was detected in thick-blood films over a 60-day period (MAb 5.2-isolated polypeptide group). These data establish that complete protective immunity to homologous challenge can be induced in Aotus monkeys using the MAb 5.2-isolated merozoite surface polypeptide.

Example 5 Cross Reactivity

Tests were performed using immunofluorescence (IFA) techniques to determine the reactivity of MAb 5.2 with polypeptides from a variety of geographical *P. falciparum* isolates. Seven different isolates were examined, as follows: Uganda Palo-Alto strain (FUP); Vietnam Oak-Knoll strain (FVO); Philippines strain (FCH-4) Cameroon strain (FCH-7); India strain (FCH-14); Papua New Guinea strain (FCH-2); Honduras strain from CDC. Immunofluorescence microscopy showed that MAb 5.2 stained the surface of merozoites derived from the seven different geographical isolates.

1. Antigen Preparation For Immunofluorescent Test

Each isolate was cultured in red blood cells in vitro at a level of 5 to 10% parasitemia. The culture, containing a majority of the parasites at the schizont stage, was suspended in PBS at pH 7.4 and centrifuged, and the process repeated again. The pellet was resuspended in Fetal Bovine Serum (v:v). Smears (containing parasitzed erythrocytes) were then made on coverslips. The smears were air dried 60 minutes at room temperature, fixed in cold acetone for 10 minutes, and wrapped and stored at −20° C. until used for the assay (or at −70° C. if stored for extended periods of time).

2. Experimental Conditions for the IFA Test

The coverslip (with smear) was brought to room temperature in a desiccator. The culture supernatant-/ascites fluid containing the hybridoma and MAb 5.2 was incubated on the antigen coverslip for 30 minutes at room temperature in a moist chamber. Three washings were conducted, 5 minutes each, with PBS at pH 7.4. This was followed by an incubation with FITC-conjugated anti-mouse IgG (H&L chain spec.) for 30 minutes at room temperature in a moist chamber. An additional three washings were conducted, 5 minutes each, with PBS. The coverslips were mounted in PBS:Glycerol, (v:v) and read using a fluorescent microscope.

3. Results

For all isolates the IFA showed that MAb 5.2 stained schizonts and merozoites with an even, linear pattern of the parasite surface. Each of the isolates gave a score of 4+, as measured on the following scale:

4+ Bright fluorescence of parasites
3+ moderate-bright fluorescence
2+ moderate fluorescence
+ weak fluorescence
− background fluorescence

What is claimed is:

1. Hybridoma cell line HB 9148 capable of producing a monoclonal antibody specific for an antigenic *Plasmodium falciparum* merozoite surface protein of approximately 185,000 dalton molecular weight.

2. The hybridoma cell line of claim 1 wherein the antigenic *Plasmodium falciparum* merozoite surface protein is from the Uganda Palo Alto FUP strain of *Plasmodium falciparum*.

3. A monoclonal antibody produced by hybridoma cell line HB 9148 and specific for an antigenic *Plasmodium falciparum* merozoite surface protein of approximately 185,000 dalton molecular weight.

4. The monoclonal antibody of claim 3 wherein the antigenic *Plasmodium falciparum* merozoite surface protein is from the Uganda Palo Alto FUP strain of *Plasmodium falciparum*.

* * * * *

UNITED STATES PATENT AND TRADEMARK OFFICE
CERTIFICATE OF CORRECTION

PATENT NO.   :   4,897,354

DATED        :   January 30, 1990

INVENTOR(S)  :   Wasim A. Siddiqui

It is certified that error appears in the above-identified patent and that said Letters Patent is hereby corrected as shown below:

Column 1, line 32, change "of" to --or--;

Column 6, line 47, after "83" change "B" to --K--;

Column 7, line 1, change "aotus" to --Aotus--;

Column 8, line 23, change "Bright" to --bright--.

Signed and Sealed this

Eighteenth Day of December, 1990

*Attest:*

HARRY F. MANBECK, JR.

*Attesting Officer*         *Commissioner of Patents and Trademarks*